US012447292B2

(12) United States Patent
Chang et al.

(10) Patent No.: US 12,447,292 B2
(45) Date of Patent: Oct. 21, 2025

(54) INHALER MONITORING ACOUSTIC BOX

(71) Applicant: I-BREATH CO., LTD., Taipei (TW)

(72) Inventors: Mou-Wei Chang, Taipei (TW); Yu-Tzu Hsu, Taipei (TW)

(73) Assignee: I-BREATH CO., LTD., Taipei (TW)

( * ) Notice: Subject to any disclaimer, the term of this patent is extended or adjusted under 35 U.S.C. 154(b) by 0 days.

(21) Appl. No.: 18/955,913

(22) Filed: Nov. 21, 2024

(65) Prior Publication Data

US 2025/0276138 A1 Sep. 4, 2025

(30) Foreign Application Priority Data

Feb. 29, 2024 (TW) ................................ 113107227

(51) Int. Cl.
*A61M 15/00* (2006.01)

(52) U.S. Cl.
CPC .... *A61M 15/0001* (2014.02); *A61M 15/0065* (2013.01); *A61M 15/008* (2014.02); *A61M 2205/3375* (2013.01)

(58) Field of Classification Search
CPC ............ A61M 15/0001; A61M 15/008; A61M 15/00; A61M 15/0065; A61M 2205/3375
See application file for complete search history.

(56) References Cited

U.S. PATENT DOCUMENTS 5,331,953 A * 7/1994 Andersson ............ A61M 15/00 128/200.14
5,505,195 A * 4/1996 Wolf ................. A61M 15/0045 128/203.14
6,076,521 A * 6/2000 Lindahl ............... A61M 15/008 128/200.23
10,272,215 B2 * 4/2019 Adams ................. A61M 11/007
2009/0308387 A1 * 12/2009 Andersen .............. A61M 15/00 128/203.15

(Continued)

FOREIGN PATENT DOCUMENTS

CA 3105148 A1 * 2/2020 ............ A61J 7/0436
TW 490308 B 6/2002

(Continued)

OTHER PUBLICATIONS

Tetsuri Kondo et al., Inhalation Flow Patterns from a Dry Powder Inhaler in Patients with Bronchial Asthma: Usefulness of a Newly-designed Handy Inhalation Profile Analyzer, Iryo Yakugaku (Japanese Journal of Pharmaceutical Health Care and Sciences), vol. 41, No. 6, pp. 388-393, 2015.

(Continued)

*Primary Examiner* — Tu A Vo

(57) ABSTRACT

Provided is an inhaler monitoring acoustic box applicable to an inhaler and including a base, a holder and a sensor. The base includes a top portion and a body portion. The top portion has a top portion opening. The body portion has a cavity, and the cavity is in communication with the outside through the top portion opening. The holder includes a fixing portion and a holding portion. The fixing portion is disposed at the top portion opening. The holding portion is connected to the fixing portion. At least one slit is formed between the holding portion and the top portion or the body portion. The sensor is disposed at the base and positioned proximate to the cavity.

8 Claims, 6 Drawing Sheets

(56) References Cited

U.S. PATENT DOCUMENTS

| | | | | |
|---|---|---|---|---|
| 2013/0008436 | A1* | 1/2013 | Von Hollen | A61M 15/009 128/200.14 |
| 2016/0051776 | A1* | 2/2016 | Von Hollen | A61M 15/0025 128/203.14 |
| 2016/0144141 | A1* | 5/2016 | Biswas | A61M 15/009 128/200.23 |
| 2017/0246406 | A1* | 8/2017 | Sutherland | A61M 15/0086 |
| 2019/0298942 | A1* | 10/2019 | Koblenski | A61B 7/003 |
| 2022/0273891 | A1* | 9/2022 | Helmlinger | G16H 40/63 |
| 2023/0120935 | A1* | 4/2023 | Davidson | A24F 40/51 |
| 2023/0168233 | A1* | 6/2023 | Srinivasan | G01N 33/0075 73/31.02 |
| 2024/0050665 | A1* | 2/2024 | Mikosz | A61M 11/00 |
| 2024/0148989 | A1* | 5/2024 | Koblenski | A61M 15/009 |
| 2024/0390612 | A1* | 11/2024 | Selby | A61M 15/008 |

FOREIGN PATENT DOCUMENTS

| | | | |
|---|---|---|---|
| TW | 201143823 | A1 | 12/2011 |
| WO | WO-2018160073 | A1 * | 9/2018 |
| WO | WO-2023123066 | A1 * | 7/2023 |

OTHER PUBLICATIONS

Martin S. Holmes et al., Acoustic Analysis of Inhaler Sounds From Community-Dwelling Asthmatic Patients for Automatic Assessment of Adherence, IEEE Journal of Translational Engineering in Health and Medicine, vol. 2, pp. 1-10, 2014, Art No. 2700210.

Terence E. Tayler et al., Objective Assessment of Patient Inhaler User Technique Using an Audio-Based Classification Approach, Scientific Reports 8:2164 (2018).

Terence E. Tayler et al., Advances in Audio-Based Systems to Monitor Patient Adherence and Inhaler Drug Delivery, Chest. Mar. 2018;153(3):710-722.

Terence E. Tayler et al., Monitoring Inhaler Inhalations Using an Acoustic Sensor Proximal to Inhaler Devices, Journal of aerosol medicine and pulmonary drug delivery. 29. 10.1089/jamp.2015.1276.

F. Tounsi et al., Electroacoustic analysis of a controlled damping planar CMOS-MEMS electrodynamic microphone, Archives of Acoustics, vol. 40, No. 4, pp. 527-537, 2015.

Terence E. Tayler et al., Estimation of inhalation flow profile using audio-based methods to assess inhaler medication adherence, PLoS One. Jan. 18, 2018;13(1):e0191330.

Shunya Takano et al., An Inhalation Device With Inertial Measurement Unit for Monitoring Inhaler Technique, IEEE/ASME Transactions on Mechatronics, vol. 27, No. 4, Aug. 2022.

Dorel Homentcovschi et al., An analytical-numerical method for determining the mechanical response of a condenser microphone, the Journal of the Acoustical Society of America, vol. 130, No. 6, pp. 3698-3705, 2011.

Winfried Möller et al., Corrections in dose assessment of 99mTc radiolabeled aerosol particles targeted to central human airways using planar gamma camera imaging, Journal of aerosol medicine and pulmonary drug delivery, vol. 22, No. 1, pp. 45-54, 2009.

Taiwan Application Serial No. 113107227, Office Action mailed May 14, 2024 and its translation.

Taiwan Application Serial No. 113107227, Claims in Response filed Jul. 4, 2024 to Office action mailed May 14, 2024 and its translation.

Taiwan Application Serial No. 113107227, Notice of Allowance mailed Sep. 27, 2024 and its translation.

* cited by examiner

X-X

INHALER MONITORING ACOUSTIC BOX

CROSS-REFERENCE TO RELATED APPLICATION

This non-provisional application claims priority under 35 U.S.C. § 119 (a) on Patent Application No(s). 113107227 filed in Taiwan, R.O.C. on Feb. 29, 2024, the entire contents of which are hereby incorporated by reference.

BACKGROUND OF THE INVENTION

1. Field of the Invention

The present disclosure relates to inhaler monitoring acoustic boxes, and in particular to an inhaler monitoring acoustic box capable of performing filtration through a mechanical structure.

2. Description of the Related Art

Owing to severe air pollution, increasingly great importance is attached to respiratory tract diseases, among which are asthma and chronic obstructive pulmonary disease (COPD) that have high prevalence rates, require long-term control, and take up a lot of medical resources. Patients with asthma or COPD are mainly treated with long-term administration of inhaled medications. Thus, the inhaled medications and inhalers applicable thereto have become important medications and medical equipment in related medical fields.

In general, inhaled medications fall into two categories: metered-dose inhalers (MDI) & soft-mist inhalers (SMI); and dry-powder inhalers (DPI). The two categories of inhaled medications are administered with their respective inhalers. Existing, common dry-powder inhalers rely on the force of patient inhalation to introduce medication powder into the inhalers and subsequently break up and atomize the powder into particles that are small enough to reach the lungs. If the force of patient inhalation is too weak, the inhaled air current will be insufficient to break up the powder for the sake of its suspension, and thus the powder cannot enter the lungs. By contrast, if the force of patient inhalation is too strong, the inhaled air current will be too fast, and the powder will enter the upper respiratory tract before being completely broken up and atomized; as a result, the powder is likely to deposit in the throat and oral cavity and thus cannot enter the lungs. In the aforesaid two situations, the medication fails to achieve therapy but causes side effects. Therefore, it is necessary to monitor and ensure that the force of patient inhalation falls within a correct range in order for the medication powder to be atomized and introduced into the lungs.

BRIEF SUMMARY OF THE INVENTION

Existing, commercially-available patient inhalation force monitoring products mostly confirm the range of the patient inhalation force by assessing sounds generated by inhalers as a result of patients' inhalation of medication. However, the sounds generated by the inhalers are weak and thus are accompanied by ambient noise during the assessment to the detriment of reading accuracy. In view of this, some manufacturers use an analog or digital circuit to process acoustic signals received by a sound reception apparatus and thereby filter out ambient noise. However, signal filtration is unsatisfactory for two reasons as follows: noise with specific directivity cannot be filtered out; and, during circuit-based or software-based filtration, if input sound contains noise, the output result will be affected by noise interference to the detriment of the detection result.

Therefore, it is an objective of the disclosure to provide an inhaler monitoring acoustic box capable of performing filtration through a mechanical structure with a view to achieving directional filtration and maintaining response strength.

To achieve the above and other objectives, the disclosure provides an inhaler monitoring acoustic box applicable to an inhaler and includes a base, a holder and a sensor. The base includes a top portion and a body portion. The top portion has a top portion opening. The body portion has a cavity, and the cavity is in communication with the outside through the top portion opening. The holder includes a fixing portion and a holding portion. The fixing portion is disposed at the top portion opening. The holding portion is connected to the fixing portion. At least one slit is formed between the holding portion and the top portion or the body portion. The sensor is disposed at the base and positioned proximate to the cavity.

In an embodiment, the top portion, the body portion or the holding portion includes a sidewall. The slit is disposed proximate to the sidewall, and the slit and the sidewall substantially extend in a vertical direction.

In an embodiment, the sensor is adapted to detect a target sound, and the slit and the target sound satisfy the relation below, $$0.5\lambda \leq l \leq 5\lambda$$

where l denotes the length of the slit, and λ denotes the wavelength of the target sound.

In an embodiment, the length of the slit is less than or equal to 150 mm and greater than or equal to 50 mm, the height of the cavity is less than or equal to 80 mm and greater than or equal to 15 mm, and the inner diameter of the cavity is less than or equal to 50 mm and greater than or equal to 20 mm.

In an embodiment, the inhaler monitoring acoustic box is further adapted to be simulated as an equivalent acoustic circuit. The sensor is adapted to detect a target sound, and the equivalent acoustic circuit structurally satisfies the relation below, $$P_{sensor}=P_{slit}+P_{cavity}+P_{radiation}+P_{membrane}+P_{back}$$

where $P_{sensor}$ denotes power generated by the target sound on the sensor, $P_{slit}$ denotes power generated by the target sound through transmission of air in the slit, $P_{cavity}$ denotes power generated by the target sound through transmission of air in the cavity, $P_{radiation}$ denotes power consumed for conversion of air sound pressure into transmission speed in air by the target sound, $P_{membrane}$ denotes power of vibration of a sensing membrane of the sensor, and $P_{back}$ denotes power consumed for compression of air near the sensor.

In an embodiment, the slit is in the number of two. The holder defines a circumferential direction, and the two slits are disposed on two opposing sides of the holding portion in the circumferential direction respectively.

In an embodiment, the inhaler monitoring acoustic box further includes an engaging member. The engaging member is connected to the fixing portion and includes at least one engaging portion. The holder defines a circumferential direction and includes a clamping portion. The clamping portion is connected to the fixing portion and has an oblique surface. The engaging member and the clamping portion are disposed on two opposing sides of the holder in the circumferential direction respectively.

In an embodiment, the holder further includes at least one resilient portion. The resilient portion and the fixing portion are engaged to the top portion and adapted to jointly enclose the inhaler.

In an embodiment, the base further includes a bottom portion. The body portion is disposed between the top portion and the bottom portion. The sensor is disposed on an inner side of the bottom portion and is in communication with an outside of the base.

In an embodiment, the inhaler monitoring acoustic box further includes a prompting unit disposed at the body portion and electrically connected to the sensor.

Therefore, when a patient is operating an inhaler, an inhaler monitoring acoustic box of the disclosure uses sound shadow effect to block high-frequency noise traveling in a specific direction and allow low-frequency sound and high-frequency target sound traveling in a specific direction to enter a cavity through a slit and thus to be received and detected by a sensor, achieving filtration through a mechanical structure.

The disclosure is illustrated by embodiments, depicted by accompanying drawings and described in detail below to render the features and advantages of the disclosure obvious and comprehensible.

BRIEF DESCRIPTION OF THE DRAWINGS

FIG. 6 is an equivalent circuit which the inhaler monitoring acoustic box in FIG. 1 is simulated as.

DETAILED DESCRIPTION OF THE INVENTION

Figure 1:
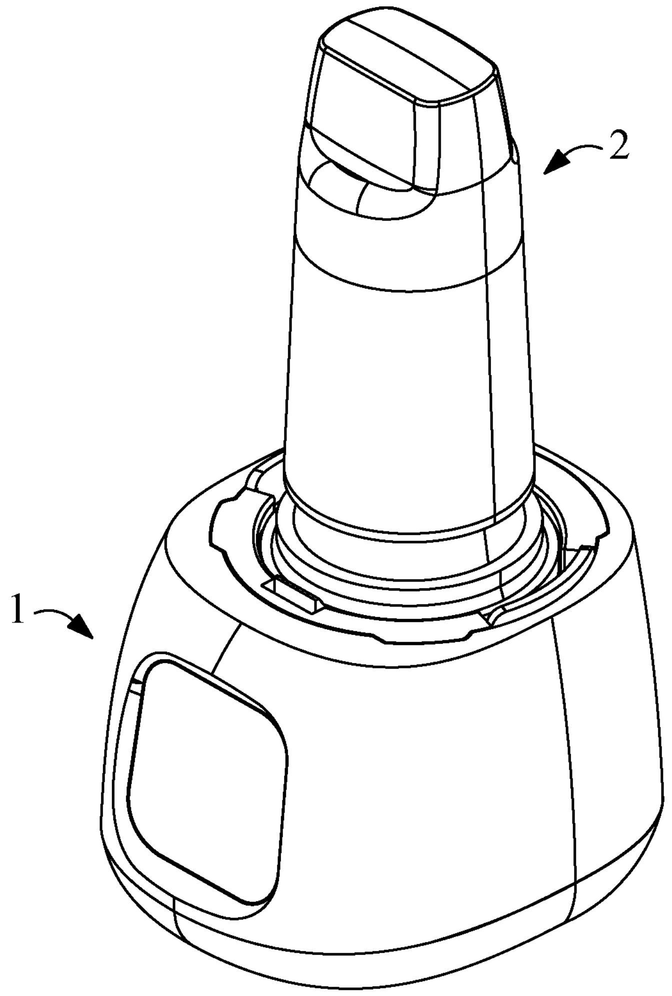
FIG. 1 is a perspective view of an inhaler monitoring acoustic box and an inhaler operating in conjunction with each other according to an embodiment of the disclosure.

The aforesaid and other technical contents, features and advantages of the disclosure are clearly presented through the detailed description of the preferred embodiments illustrated by the accompanying drawings. Direction-related terms used in the embodiments below, such as "upper", "lower", "left", "right", "front" and "rear", are intended to refer to the directions depicted in accompanying drawings. The direction-related terms are aimed at assisting with describing and understanding the embodiments of the disclosure rather than limiting the disclosure. Identical or similar components in the embodiments below are denoted by identical or similar reference numerals.

Figure 2:
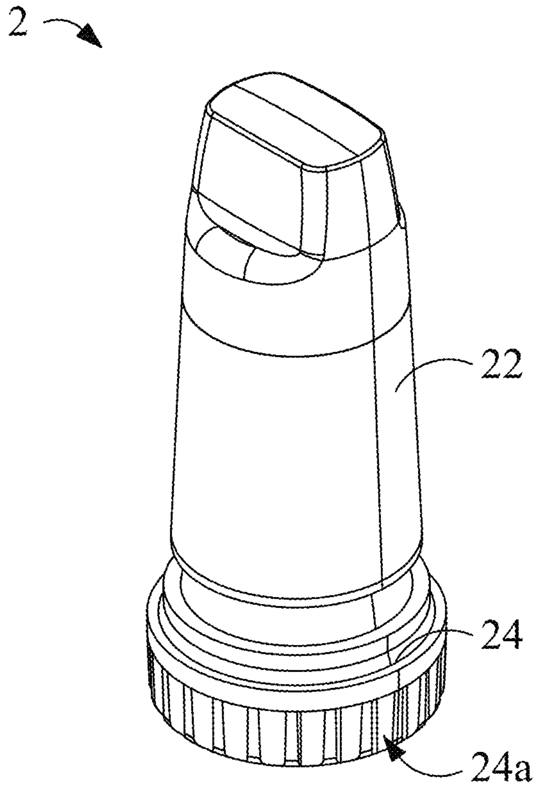
FIG. 2 is a perspective view of the inhaler in FIG. 1.

Refer to FIG. 1 and FIG. 2. FIG. 1 is a perspective view of an inhaler monitoring acoustic box 1 and an inhaler 2 operating in conjunction with each other according to an embodiment of the disclosure. FIG. 2 is a perspective view of the inhaler 2 in FIG. 1. In this embodiment, the inhaler monitoring acoustic box 1 is applicable to the inhaler 2. The inhaler 2 is, for example, a dry-powder inhaler for receiving Symbicort Rapihaler. The inhaler monitoring acoustic box 1 corresponds in size to the inhaler 2, and thus a user is able to conveniently take and hold the inhaler monitoring acoustic box 1 and the inhaler 2 together when the inhaler 2 is fitted to the inhaler monitoring acoustic box 1. As shown in FIG. 2, the inhaler 2 includes a body 22 and a bottom 24. The bottom 24 connects to the body 22 and includes a plurality of close-fit features 24*a*. The close-fit features 24*a* are, for example, ribs disposed on the surface of the bottom 24 and spaced apart from each other equidistantly.

Figure 3:
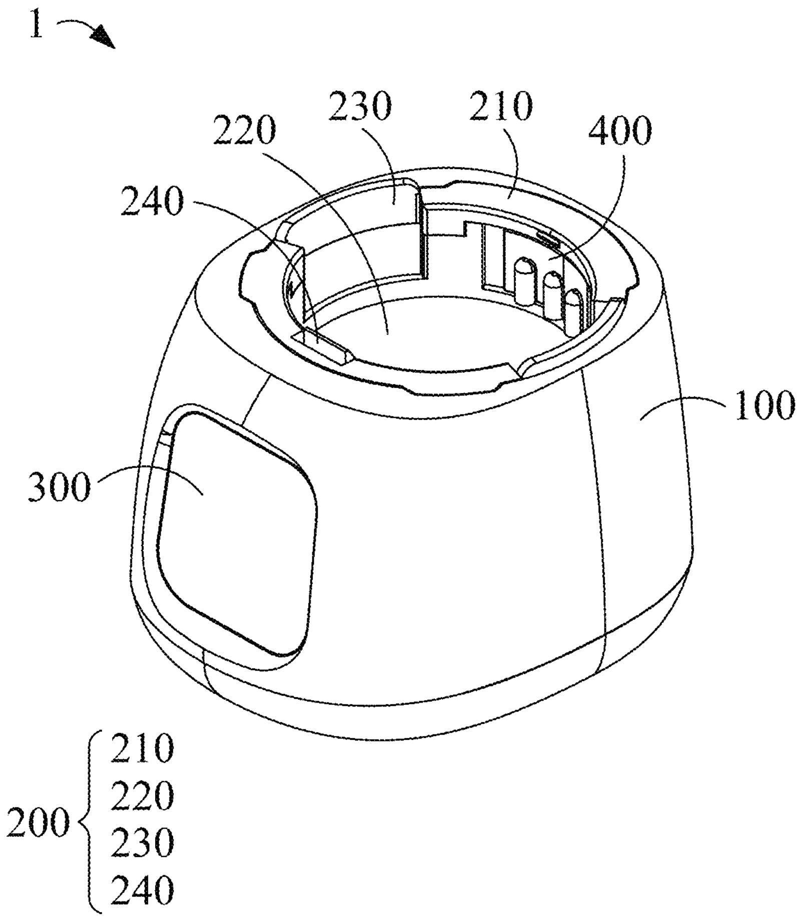
FIG. 3 is a perspective view of the inhaler monitoring acoustic box in FIG. 1.
Figure 4:
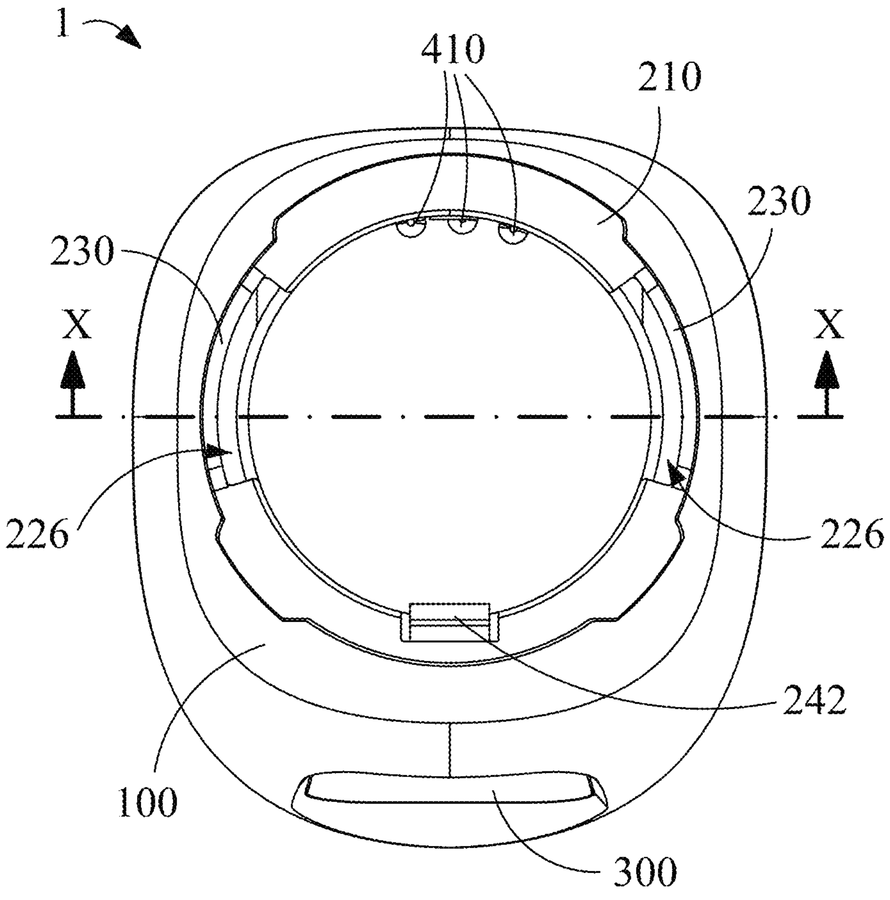
FIG. 4 is a top view of FIG. 3.
Figure 5:
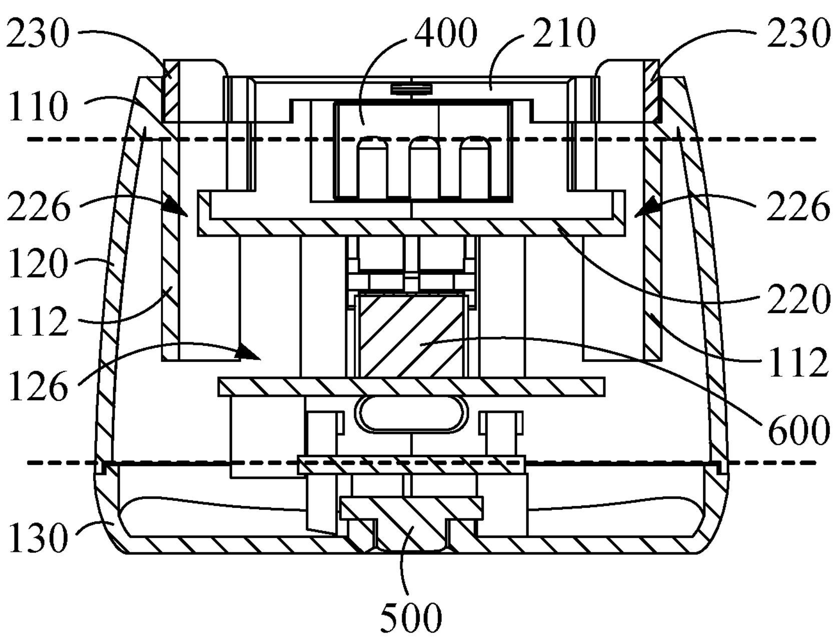
FIG. 5 is a cross-sectional view taken along line X-X of FIG. 4.

Refer to FIG. 3 through FIG. 5. FIG. 3 is a perspective view of the inhaler monitoring acoustic box 1 in FIG. 1. FIG. 4 is a top view of FIG. 3. FIG. 5 is a cross-sectional view taken along line X-X of FIG. 4. In this embodiment, the inhaler monitoring acoustic box 1 includes a base 100, a holder 200 and a sensor 500. The base 100 blocks ambient noise and has a chamber for transmitting the sound generated by the inhaler 2. The holder 200 is disposed on the base 100 and adapted to hold the inhaler 2. The sensor 500 is, for example, a microphone connected to a digital circuit and adapted to receive sound generated by air passing through the internal space of the base 100 and then convert the sound into a signal to be read by the system.

The base 100 includes a top portion 110, a body portion 120 and a bottom portion 130 (which are separated by dashed lines in FIG. 5.) The top portion 110 has a top portion opening. The body portion 120 has a cavity 126, and the cavity 126 is in communication with the outside through the top portion opening. The bottom portion 130 has a bottom portion opening. The holder 200 defines a circumferential direction and includes a fixing portion 210 and a holding portion 220. The fixing portion 210 is, for example, substantially ring-shaped and disposed at the top portion opening. The holding portion 220 connects to the fixing portion 210. At least one slit 226 is formed between the holding portion 220 and the top portion 110 or the body portion 120. In this embodiment, for example, the slit 226 is formed between the top portion 110 and the holding portion 220 and is in the number of two, allowing the slits 226 to be disposed on two opposing sides of the holding portion 220 in the circumferential direction respectively, but the disclosure is not limited thereto. In a variant embodiment, only one slit 226 is provided according to the sound-emitting position of the inhaler 2, or a plurality of slits 226 are aligned in the circumferential direction of the holding portion 220 and arranged asymmetrically. The sensor 500 is disposed at the bottom portion opening.

Ambient noise is likely to interfere with a sound sensor detecting the sound generated by a gas being inhaled into the inhaler 2 and thereby distort the detection result while the user is inhaling medication with the inhaler 2. Conventional circuit-based filtration entails processing original sound signals of background noise and thus is disadvantaged by high computation cost and incomplete filtration. In this embodiment, the slit 226 is formed between the base 100 and the holder 200 of the inhaler monitoring acoustic box 1, the sound generated by the user inhaling medication through the inhaler 2 causes synchronous resonance of air in the vicinity of the slit 226 and air in the cavity 126 of the base 100 and thus is detected by the sensor 500. In this embodiment, not only is the sound generated by the user inhaling medication directly detected by the sensor 500, but lateral noise is also blocked by the top portion 110, the body portion 120 and the holding portion 220 and thus prevented from entering the cavity 126 to otherwise interfere with the detection result of the sensor 500.

As shown in FIG. 5, the top portion 110 includes sidewalls 112 corresponding in number to the slits 226, with the slits 226 positioned proximate to the sidewalls 112, allowing the slits 226 and the sidewalls 112 to substantially extend in the vertical direction (i.e., in the top-bottom direction in FIG. 5).

Thus, only the sound that travels squarely toward the slits 226 can be transmitted through vertical vibration of air at the corresponding position, whereas the sound traveling in the direction perpendicular to the sidewalls 112 is blocked. Therefore, directional reception of sound can be achieved.

Figure 6:
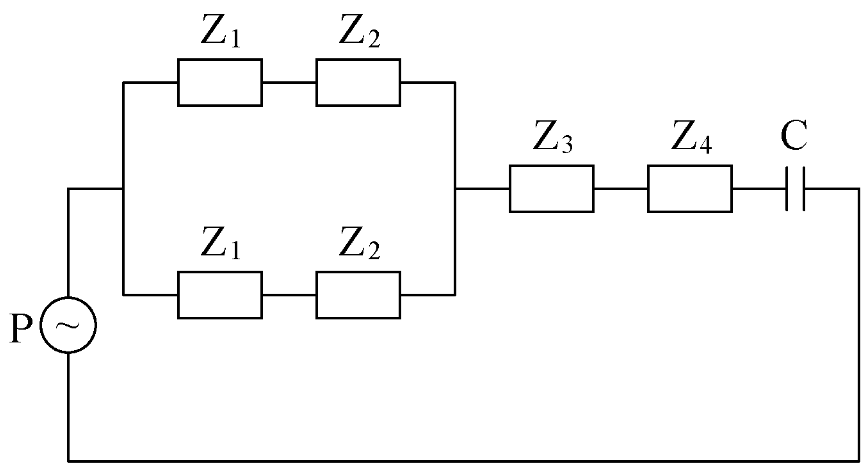

Referring to FIG. 6, there is shown an equivalent circuit which the inhaler monitoring acoustic box 1 in FIG. 1 is simulated as. The inhaler monitoring acoustic box 1 is simulated as an equivalent circuit from which the relation below is derived.

$$P_{sensor}=P_{slit}+P_{cavity}+P_{radiation}+P_{membrane}+P_{back}$$

$P_{sensor}$ denotes the power generated by target sound on the sensor 500. $P_{slit}$ denotes the power generated by target sound through transmission of air in the slits 226. $P_{cavity}$ denotes the power generated by target sound through transmission of air in the cavity 126. $P_{radiation}$ denotes the power consumed for conversion of air sound pressure into transmission speed in air by target sound. $P_{membrane}$ denotes the power of vibration of a sensing membrane of the sensor 500. $P_{back}$ denotes the power consumed for compression of air near the sensor 500.

The model can be simplified through "grounding" all the air inside the inhaler monitoring acoustic box 1 by placing the sensor 500 at the bottom portion opening to not only allow the sensor 500 to be disposed on the inner side of the bottom portion 130 but also allow the sensor 500 to be in communication with the outside of the base 100, allowing the pressure difference between the former and the latter to be equal to the pressure difference between atmospheric pressure subjected to the transmission of target sound and atmospheric pressure subjected to vibration. In this situation, the air inside the inhaler monitoring acoustic box 1 in the "non-vibrating, solely-compressed" mode is simulated as a capacitor in the circuit, with its corresponding impedance expressed by equations as follows:

$$Z_C \approx \frac{1}{j\omega C}$$

$$C = \frac{V}{\rho_0 c^2}$$

$$V = SL$$

$Z_C$ denotes the impedance when the air in the acoustic box (including the cavity 126 and the slits 226) functions as a capacitor subjected to compression. ω denotes angular frequency of target sound. C denotes equivalent capacitance. V denotes equivalent volume of air. $\rho_0$ denotes air density. S denotes cross-sectional area of the corresponding portion. L denotes the length of the air in the vertical direction. c denotes the speed of sound in air.

The two ends of the air in the slit 226 are free ends. Thus, except for capacitive expression, the "non-compressed, solely-vibrating" mode is simulated as an inductor in the circuit, with its corresponding impedance expressed by equations as follows:

$$Z_L \approx j\omega M_A$$

$$M_A = \frac{\rho_0 L}{S}$$

$Z_L$ denotes the impedance when the air in the slit 226 functions as an inductor and vibrates. $M_A$ denotes the acoustic mass of the aforesaid air. Low-frequency noise facing the slits 226 can be filtered out by adjusting the length of the slits 226. The height of existing, commercially-available monitoring acoustic boxes ranges from a half wavelength of target sound to five wavelengths of target sound, allowing the target sound and the slits 226 of the inhaler monitoring acoustic box 1 to satisfy the relation below.

$$0.5\lambda \leq l \leq 5\lambda$$

λ denotes the wavelength of target sound. l denotes the length of the slits 226 in the vertical direction. However, conventional simulation cannot be accurately applicable to the aforesaid situation. The slits 226 and the cavity 126 are jointly simulated as an acoustically-dedicated T-shaped circuit through a mechanical structure to perform filtration through the intrinsic structure of the acoustic box-a major feature that conventional digital circuit filtration cannot achieve.

The air sound pressure is converted into a transmission speed in air by target sound. Since the product of the surface radius of the microphone of the sensor 500 and the wave number of the target sound is much less than 1, the impedance (also known as radiation impedance) corresponding to the transmission speed at the input end of the sensor 500 is expressed by the equations below.

$$Z_{rad} = R_r + jX_r \approx R_r + j\omega M_r$$

$$R_r = \pi a^2 \rho_0 c R_1(2ka) \approx \frac{1}{2}\pi a^2 \rho_0 c (ka)^2$$

$$M_r \approx \frac{X_r}{\omega} \approx \frac{\rho_0 \pi a^2}{8a/3\pi}$$

$$k = \frac{2\pi}{\lambda}$$

$Z_{rad}$ denotes radiation impedance; $R_r$ denotes impedance real component (equivalent resistance); $X_r$ denotes impedance imaginary component and thus approximates to the product of angular frequency and equivalent inductance $M_r$; k denotes wave number; a denotes feature dimension radius of target area. When the inhaler 2 generates any one instance of sound, the sound enters the cavity 126 through any one of the slits 226 and is then received by the sensor 500. Therefore, impedance of the slits 226 (including inductance configuration and capacitance configuration), impedance of the cavity 126 (including inductance configuration and capacitance configuration), radiation impedance, impedance of the sensor 500 and capacitance of air outside the sensor 500 correspond to first impedance $Z_1$, second impedance $Z_2$, third impedance $Z_3$, fourth impedance $Z_4$ and equivalent capacitance C respectively, and the power of target sound correspond to equivalent power P, building an equivalent circuit shown in FIG. 6.

In the entire equivalent circuit, the impedance of the cavity 126, radiation impedance, the impedance of the sensor 500 and equivalent capacitance C which external air is simulated as can be regarded as constant and invariable. Thus, first impedance $Z_1$ is adjusted to receive and amplify sound of a specific frequency by adjusting different sizes of the slits 226. Therefore, when different users use different inhalers 2 and thus necessitate detection of different inhalation force ranges or set a detection segment to a specific frequency, this can be achieved by adjusting the slits 226 of the inhaler monitoring acoustic box 1, enhancing the flexibility of the use of the inhaler monitoring acoustic box 1.

The length of the slit 226 is preferably less than or equal to 150 mm and greater than or equal to 50 mm to ensure that viscosity resistance of the air passing through the slits 226 can be ignored in the entire course of circuit simulation. When the slit 226 is in a plural number, the length is equal to the sum of the lengths of the slits 226. The height of the cavity 126 is preferably less than or equal to 80 mm and greater than or equal to 15 mm, and the inner diameter of the cavity 126 is less than or equal to 50 mm and greater than or equal to 20 mm. Substitution of the relations further results in the relation presented below and related to acoustic mass of air in the slits 226.

$$M_A = 0.27\frac{\rho_o}{\alpha}$$

To adjust the slits 226 conveniently, in this embodiment, the holder 200 further includes at least one resilient portion 230. The resilient portion 230 is, for example, a ring-shaped structure positioned outside the radial direction of the holder 200 relative to the fixing portion 210 and exhibiting resilience. The resilient portion 230 is, for example, in the number of two and thus are disposed on two opposing sides of the holder 200 in the circumferential direction respectively. The resilient portion 230 and the fixing portion 210 are fitted to the top portion 110. The resilient portion 230 and the fixing portion 210 are adapted to jointly enclose the inhaler 2 as soon as the inhaler monitoring acoustic box 1 and the inhaler 2 are fitted together. Therefore, when the user needs the slits 226 of different sizes to attain different inhalation forces or frequencies, the user presses the resilient portion 230 to separate the holder 200 from the base 100 and mount the holder 200 of another type on the base 100 to change the size of the slits 226, attaining the intended inhalation forces and frequencies.

In some feasible embodiments, the inhaler monitoring acoustic box 1 further includes an engaging member 400 connected to the fixing portion 210 and including at least one engaging portion 410. In this embodiment, the engaging portion 410 is, for example, capsule-shaped and corresponds in position to the close-fit features 24*a* of the bottom 24. The holder 200 further includes a clamping portion 240. The clamping portion 240 is, for example, a resilient hook-shaped leaf spring and has an oblique surface 242. The engaging member 400 and the clamping portion 240 are disposed on two opposing sides of the holder 200 in the circumferential direction respectively. Therefore, to fit the inhaler 2 to the inhaler monitoring acoustic box 1, the user allows the bottom 24 to enter the fixing portion 210 smoothly under the guidance of the oblique surface 242 so as to be held by the holding portion 220. After the inhaler 2 has been fitted to the inhaler monitoring acoustic box 1, the clamping portion 240 which has been resiliently dislocated under a force rebounds and thereby clamps the bottom 24 axially through the hook-shaped structure; meanwhile, the engaging portion 410 is fitted in place between the close-fit features 24*a* to prevent the rotation of the inhaler 2 relative to the holder 200 in the circumferential direction and thereby preclude the displacement of the inhaler monitoring acoustic box 1 and the inhaler 2 relative to each other.

In this embodiment, the engaging member 400 is disposed on one side of the holder 200, and the clamping portion 240 is disposed on the other side of the holder 200, fixing the inhaler 2 in place, but the disclosure is not limited thereto. In some other feasible embodiments, the engaging member 400 and the engaging portion 410 are spaced apart from each other equidistantly in the circumferential direction, or the clamping portions 240 are provided in a plural number to coordinate with additional ribs aligned in the circumferential direction, fixing the inhaler 2 in place.

Preferably, as shown in FIG. 3 and FIG. 5, the inhaler monitoring acoustic box 1 further includes a prompting unit 300 and a control unit 600. The prompting unit 300 is, for example, a liquid crystal display panel disposed at the body portion 120. The control unit 600 is, for example, a processor. The prompting unit 300 is electrically connected to the sensor 500 through the control unit 600. Therefore, when the magnitude of the inhalation force is lower or higher than a predetermined threshold, signals outputted by the sensor 500 are read by the control unit 600, so as for the prompting unit 300 to display an alert message in real time, optimizing the efficacy of inhaled medications by informing the user of the need to increase or decrease the magnitude of the inhalation force.

Therefore, in this embodiment, the base 100 and the slit 226 of the inhaler monitoring acoustic box 1 operate in conjunction with each other to not only block lateral noise but also restrict admittance to the sound facing the slit 226, achieving directional reception of target sound. Moreover, the size of the slit 226 can be adjusted to receive target sound under different inhalation forces and at different frequencies, adjust the length of the slit 226 appropriately, further filter out low-frequency noise in target sound, and filter out high-frequency noise easily because of a great difference in frequencies between the high-frequency noise and target sound, enhancing the detection capability of the inhaler monitoring acoustic box 1 greatly.

The disclosure is disclosed above by preferred embodiments. However, persons skilled in the art should understand that the embodiments are illustrative of the disclosure only, but shall not be interpreted as restrictive of the scope of the disclosure. Thus, all variations and replacements equivalent to the embodiments shall be deemed falling within the scope of the disclosure, and technical features of the embodiments can be appropriately combined, replaced, dispensed with and changed on condition that neither conceptual contradictions nor structural conflicts arise. Therefore, the legal protection for the disclosure shall be defined by the appended claims.

While the present disclosure has been described by means of specific embodiments, numerous modifications and variations could be made thereto by those skilled in the art without departing from the scope and spirit of the present disclosure set forth in the claims.

What is claimed is:

1. An inhaler monitoring acoustic box, applicable to an inhaler, comprising:

a base, comprising:
  a top portion having a top portion opening; and
  a body portion having a cavity in communication with an outside through the top portion opening;
a holder, comprising:
  a fixing portion disposed at the top portion opening; and
  a holding portion connected to the fixing portion, with at least one slit formed between the holding portion and the top portion or the body portion; and
a sensor disposed at the base and positioned proximate to the cavity,
wherein the top portion, the body portion or the holding portion comprises a sidewall, the at least one slit is disposed proximate to the sidewall, and the at least one slit and the sidewall substantially extend in a vertical direction; and wherein the sensor is adapted to detect a target sound, and the at least one slit and the target sound satisfy a relation below, $$0.5\lambda \leq l \leq 5\lambda$$

where ι denotes a length of the at least one slit, and λ denotes a wavelength of the target sound.

2. The inhaler monitoring acoustic box of claim 1, wherein the length of the at least one slit is less than or equal to 150 mm and greater than or equal to 50 mm, a height of the cavity is less than or equal to 80 mm and greater than or equal to 15 mm, and an inner diameter of the cavity is less than or equal to 50 mm and greater than or equal to 20 mm.

3. The inhaler monitoring acoustic box of claim 1, being further adapted to be simulated as an equivalent acoustic circuit, the sensor being adapted to detect a target sound, and the equivalent acoustic circuit to structurally satisfy a relation below, $$P_{sensor}=P_{slit}+P_{cavity}+P_{radiation}+P_{membrane}+P_{back}$$

where $P_{sensor}$ denotes power generated by the target sound on the sensor, $P_{slit}$ denotes power generated by the target sound through transmission of air in the at least one slit, $P_{cavity}$ denotes power generated by the target sound through transmission of air in the cavity, $P_{radiation}$ denotes power consumed for conversion of air sound pressure into transmission speed in air by the target sound, $P_{membrane}$ denotes power of vibration of a sensing membrane of the sensor, and $P_{back}$ denotes power consumed for compression of air near the sensor.

4. The inhaler monitoring acoustic box of claim 1, wherein the at least one slit is in the number of two, the holder defines a circumferential direction, and the two slits are disposed on two opposing sides of the holding portion in the circumferential direction respectively.

5. The inhaler monitoring acoustic box of claim 1, further comprising:

an engaging member connecting to the fixing portion and comprising at least one engaging portion, wherein the holder defines a circumferential direction and comprises a clamping portion, the clamping portion is connected to the fixing portion and comprises an oblique surface, and the engaging member and the clamping portion are disposed on two opposing sides of the holder in the circumferential direction respectively.

6. The inhaler monitoring acoustic box of claim 1, wherein the holder further comprises at least one resilient portion, the at least one resilient portion and the fixing portion are engaged to the top portion and adapted to jointly enclose the inhaler.

7. The inhaler monitoring acoustic box of claim 1, wherein the base further comprises a bottom portion, the body portion is disposed between the top portion and the bottom portion, and the sensor is disposed on an inner side of the bottom portion and is in communication with an outside of the base.

8. The inhaler monitoring acoustic box of claim 1, further comprising a prompting unit disposed at the body portion and electrically connected to the sensor.

* * * * *